United States Patent
Grossman

(10) Patent No.: US 11,812,804 B2
(45) Date of Patent: Nov. 14, 2023

(54) DECUBITUS ULCERS PREVENTION GARMENT

(71) Applicant: Leonid Grossman, Centennial, CO (US)

(72) Inventor: Leonid Grossman, Centennial, CO (US)

( * ) Notice: Subject to any disclaimer, the term of this patent is extended or adjusted under 35 U.S.C. 154(b) by 60 days.

(21) Appl. No.: 17/749,786

(22) Filed: May 20, 2022

(65) Prior Publication Data

US 2022/0369738 A1   Nov. 24, 2022

Related U.S. Application Data

(60) Provisional application No. 63/191,427, filed on May 21, 2021.

(51) Int. Cl.

| A61F 13/06 | (2006.01) |
| A41D 13/05 | (2006.01) |
| A61F 5/34 | (2006.01) |
| A41D 13/12 | (2006.01) |
| A41D 13/018 | (2006.01) |
| A61F 13/14 | (2006.01) |

(52) U.S. Cl.
CPC ....... *A41D 13/1254* (2013.01); *A41D 13/018* (2013.01); *A41D 13/0506* (2013.01); *A61F 5/34* (2013.01); *A61F 13/14* (2013.01); *A61F 13/069* (2013.01)

(58) Field of Classification Search
CPC . A61F 13/069; A61F 5/30; A61F 5/34; A41D 13/1254; A41D 13/018; A41D 13/0506
See application file for complete search history.

(56) References Cited

U.S. PATENT DOCUMENTS

| 4,089,065 | A | 5/1978 | McGee |
| 4,370,754 | A | 2/1983 | Donzis |
| 4,453,271 | A | 6/1984 | Donzis |
| 4,737,994 | A | 4/1988 | Galton |
| 5,551,082 | A | 9/1996 | Stewart et al. |
| 5,636,377 | A | 6/1997 | Wiener |
| 5,830,164 | A | 11/1998 | Cone et al. |
| 6,859,948 | B2 | 3/2005 | Melts |
| 8,052,630 | B2 | 11/2011 | Kloecker et al. |
| 8,161,916 | B2 * | 4/2012 | Bertocci ............... A61D 9/00 119/850 |
| 9,381,340 | B2 * | 7/2016 | Mushahwar ......... A61N 1/0492 |
| 2003/0135917 | A1 * | 7/2003 | Ruane ............... A41D 13/0506 2/465 |

(Continued)

*Primary Examiner* — Camtu T Nguyen

(74) *Attorney, Agent, or Firm* — Maier & Maier, PLLC

(57) ABSTRACT

A decubitus ulcers prevention garment for decreasing the skin pressure on a select body area of the population at risk for decubitus may be provided. The garment may be similar in shape to boxer briefs and composed of strategically mapped air cells for the patients' bilateral hips, proximal thighs and gluteal region wrapping posteriorly, targeting anatomic points including greater trochanteric, ischial tuberosities, posterior iliac spines, sacrum and coccyx. The air cell arrangement may allow for patterned inflation and deflation thereby offloading and loading particular areas. As air cells are cycled through inflation and deflation, skin pressure may be decreased thereby preventing focal pressure and local tissue ischemia resulting in necrosis.

5 Claims, 1 Drawing Sheet

(56) References Cited

U.S. PATENT DOCUMENTS

| | | | |
|---|---|---|---|
| 2004/0147863 A1* | 7/2004 | Diaz | A61F 15/008 |
| | | | 602/41 |
| 2004/0168245 A1 | 9/2004 | Goodwin | |
| 2005/0154336 A1 | 7/2005 | Kloecker et al. | |
| 2005/0261656 A1 | 11/2005 | Garcia et al. | |
| 2006/0064800 A1* | 3/2006 | Freund | A61F 13/069 |
| | | | 2/446 |
| 2007/0186328 A1* | 8/2007 | Bulian | A41D 1/084 |
| | | | 2/69 |
| 2007/0277282 A1* | 12/2007 | Sheppell | A41D 13/1236 |
| | | | 2/69 |
| 2009/0194115 A1* | 8/2009 | Squitieri | A61F 13/069 |
| | | | 128/889 |
| 2009/0260639 A1* | 10/2009 | Hsu | A61F 13/0226 |
| | | | 602/60 |
| 2010/0051037 A1 | 3/2010 | Hong et al. | |
| 2014/0173812 A1* | 6/2014 | Krueger | A41D 13/0155 |
| | | | 2/455 |

\* cited by examiner

DECUBITUS ULCERS PREVENTION GARMENT

BACKGROUND

In order to serve the population at risk for decubitus, including those with neurologic or cognitive deficits which prevent repositioning and causing local tissue ischemia, common decubitus ulcers prevention devices focus on the structure the patient is on, for example, a wheelchair cushion or an inflatable or repositioning bed. However, those devices do not target known areas of concern and only provide static measurements for wound suppression. In addition, those devices are not worn and do not allow for intimate position near the areas of concern therefore they are unable to effectively off load those areas.

Therefore, there is a need for an effective decubitus ulcers prevention device for decreasing the skin pressure on a select body area of the population at risk for decubitus, especially the patients' bilateral hips, proximal thighs and gluteal region wrapping posteriorly, targeting anatomic points including greater trochanteric, ischial tuberosities, posterior iliac spines, sacrum and coccyx.

SUMMARY

The embodiments relate generally to a decubitus ulcers prevention garment similar in shape to boxer briefs composed of strategically mapped air cells for the patients' bilateral hips, proximal thighs and gluteal region wrapping posteriorly, targeting anatomic points including greater trochanteric, ischial tuberosities, posterior iliac spines, sacrum and coccyx, whose arrangement allows for patterned inflation and deflation thereby off loading and loading particular areas.

DETAILED DESCRIPTION OF THE EMBODIMENTS

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Figure 1:
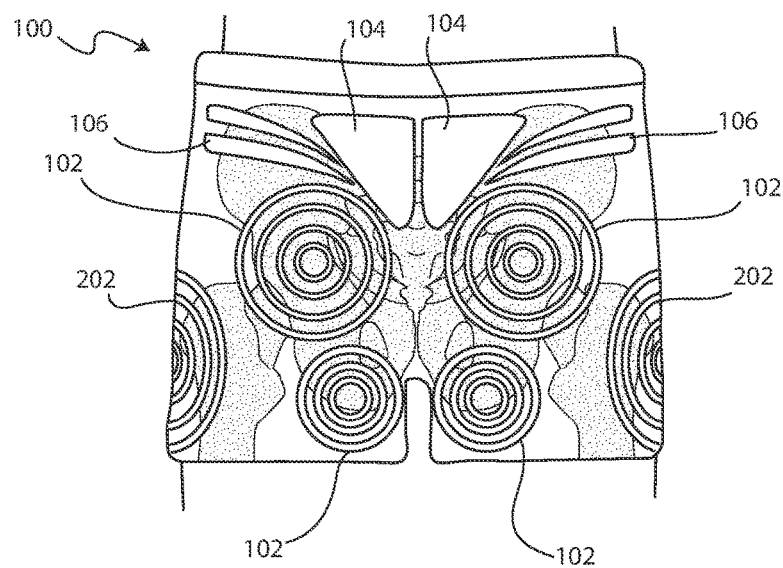
FIG. 1 is an exemplary diagram showing the back of a decubitus ulcers prevention garment with air cells.

Referring generally to exemplary FIG. 1, embodiments described herein may relate to a decubitus ulcers prevention garment 100 with air cells 102/104/106. The decubitus ulcers prevention garment can be similar in shape to boxer briefs. The air cells can be generically mapped to standard pressure points of patient which including greater trochanters, ischial tuberosities, posterior iliac spines, sacrum and coccyx. For example, FIG. 1 illustrates an exemplary embodiment which may include two sets of air cells 102 arranged in a circular or spiral arrangement over the posterior. The circular air cells 102 may be split into multiple pockets or sections to allow some portion of the air cells to inflate independent of others. As shown in FIG. 1, each set of air cells 102 may cover the ischial tuberosities, a portion or half of the sacrum and/or coccyx. Multiple sets of air cells 102 may be included on an exemplary embodiment. For example, air cells 102 may be placed over each ischial tuberosity and each side of the ilium or iliac spines. Triangular air cells 104 may be included around the sacrum. Additional air cells 106 may surround the posterior portion of the garment. Alternatively, pressure points can be mapped specifically to a patient's unique disposition.

In some embodiments, the air cells can be arranged centered over the patients' bilateral hips, proximal thighs and gluteal region wrapping posteriorly (targeting anatomic points including greater trochanteric, ischial tuberosities, posterior iliac spines, sacrum and coccyx) with successively larger air cells. Further, while the air cells are shown as rings or otherwise circular, it may be appreciated that different embodiments may utilize air cells having different sizes or shapes in order to provide more targeted, dispersed, or otherwise patient-centric treatment or therapy.

In some embodiments, the anterior part of the decubitus ulcers prevention garment can be composed of mess or material which does not need to have structure for air cells.

In some embodiments, air cells can be arranged around the sacrum. The air cells around the sacrum 104 may be triangular in shape, mirroring the shape of the sacrum. An exemplary embodiment may include two triangular air cells or two triangular sets of air cells which together may mirror the triangular shape of the sacrum.

In some embodiments, the air cells around the sacrum can be separated on the right and left sides to allow for separate control.

Figures 2, 3:
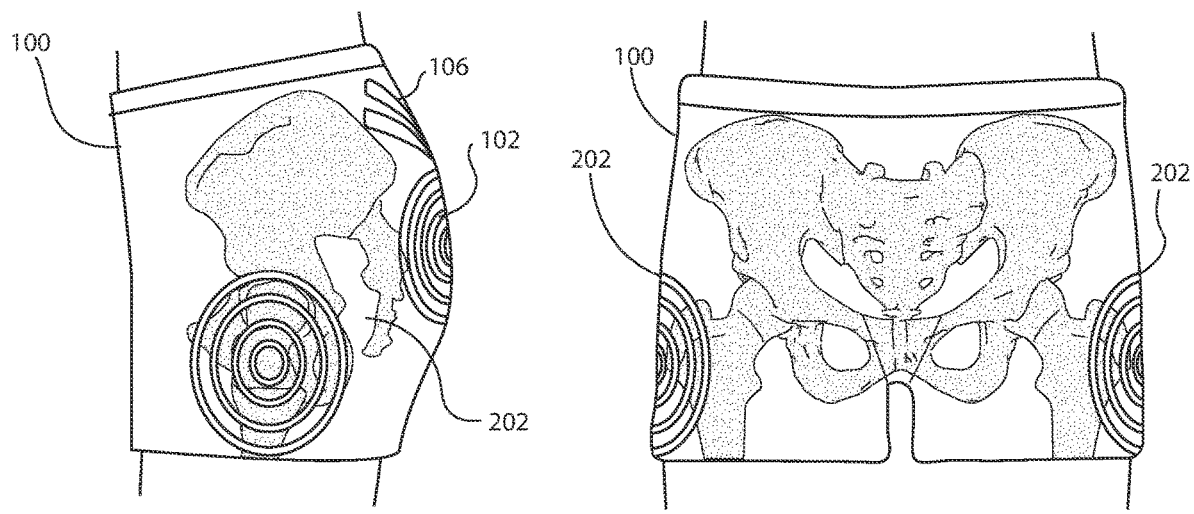
FIG. 2 is an exemplary diagram showing the side of a decubitus ulcers prevention garment with air cells.
FIG. 3 is an exemplary diagram showing the front of a decubitus ulcers prevention garment with air cells.

The exemplary embodiment in FIG. 2 may illustrate a side view of an exemplary garment. An exemplary embodiment may include one or more air cells around the side of the garment. For example, the air cells may be placed over the iliac spines or crest on either side of the wearer. In the exemplary embodiment illustrated in FIG. 2, the side air cells 202 depicted are circular in order to target a large portion of the iliac crest and spines, but other shapes may be contemplated.

In some embodiments, the air cell arrangement can allow for patterned inflation and deflation thereby off loading and loading particular areas. Pattern of the air cell inflation can be controlled by an electronic control unit temporally or by pressure transducers. As the air cells are cycled through inflation and deflation, skin pressure is decreased thereby preventing focal pressure and local tissue ischemia.

In some embodiments, material for the decubitus ulcers prevention garment can be composed of welded sheet plastic and felted or softened on inside layer to prevent abrasion.

In some embodiments, the decubitus ulcers prevention garment can be connected to a motor unit that allows for multiple hoses and multiple valves to target the air cell pockets of interest for inflation and deflation.

Referring now to FIG. 3, the exemplary embodiment in FIG. 3 may illustrate a front-view of an exemplary garment. In some embodiments, the decubitus ulcers prevention garment can be made disposable and multiple sizes to fit individuals. In additional, the garment can be made oversized in the front in order to allow diapers or additional hygiene devices to be placed underneath.

As a result, it may be appreciated that decreasing the skin pressure of a select body area thereby preventing focal pressure and local tissue ischemia may be achieved.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A decubitus ulcers prevention garment for a patient comprising:

at least two sets of circular-shaped air cells, wherein one set of circular-shaped air cells is configured to cover at least one of an ischial tuberosity and a portion of a sacrum;

at least two triangular-shaped air cells mirror each other and mirroring the sacrum, wherein the at least two triangular-shaped air cells are configured to cover the sacrum; and wherein each of the at least two sets of circular-shaped air cells comprises a plurality of ring-shaped air cells arranged in concentric configuration, wherein each circular-shaped air cell is configured to inflate or deflate independently.

2. The decubitus ulcer prevention garment of claim 1, further comprising a plurality of additional air cells surrounding a posterior portion of the decubitus ulcer prevention garment.

3. The decubitus ulcer prevention garment of claim 1, further comprising a felted layer on an inside surface of the decubitus ulcer prevention garment.

4. The decubitus ulcer prevention garment of claim 1, further comprising a plurality of additional air cells adapted to be mapped to pressure points on at least one the sacrum, the ischial tuberosity, posterior iliac spines, coccyx, and greater trochanters.

5. The decubitus ulcer prevention garment of claim 1, wherein the decubitus ulcer prevention garment is formed from a welded plastic sheet and a softened layer.

* * * * *